US006579689B2

(12) United States Patent
Cordell et al.

(10) Patent No.: US 6,579,689 B2
(45) Date of Patent: Jun. 17, 2003

(54) MODULATION OF γ-SECRETASE ACTIVITY

(75) Inventors: Barbara Cordell, Palo Alto, CA (US); Jeffrey N. Higaki, Mountain View, CA (US); Mitchell Mutz, Palo Alto, CA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/852,914

(22) Filed: May 9, 2001

(65) Prior Publication Data

US 2001/0055782 A1 Dec. 27, 2001

Related U.S. Application Data

(60) Provisional application No. 60/203,506, filed on May 11, 2000.

(51) Int. Cl.[7] ...................... G01N 33/53; G01N 33/537; C12N 9/00; C12N 9/14

(52) U.S. Cl. ...................... 435/7.92; 435/183; 435/195; 435/219; 530/350

(58) Field of Search ................................. 435/7.92, 183, 435/219; 530/300, 350; 800/12

(56) References Cited

FOREIGN PATENT DOCUMENTS

| EP | 0 778 266 | 11/1997 |
|---|---|---|
| WO | WO 97/41443 | 11/1997 |
| WO | WO 98/15828 | 4/1998 |
| WO | WO 01/16355 | 3/2001 |
| WO | WO 01/49871 | 7/2001 |
| WO | WO 01/75435 | 10/2001 |

OTHER PUBLICATIONS

Xu et al., 1997, Proc. Natl. Acad. Sci., USA, 94, pp. 3748–3752.*
Annaert et al. (1999) "Presenilins: molecular switches between proteolysis and signal transduction." *TINS*, 22(10):439–443.
Chakrabarti et al. (1985) "Vaccinia virus expression vector: coexpression of beta–galactosidase provides visual screening of recombinant virus plaques." *Mol. Cell Biol.*, vol. 5:3403–9.
Checler (1995) "Processing of the beta–amyloid precursor protein and its regulation in Alzheimer's disease." *J. Neurochem.*, vol. 65:1431–1444.
Clark et al. (1993) "Molecular genetics of Alzheimer's disease." *Arch. Neurol.*, vol. 50:1164–1172.
Cochran et al. (1985) "Eukaryotic transient expression system dependent on transcription factors and regulatory DNA sequences of vaccinia virus." *Proc. Natl. Acad. Sci. USA*, vol. 82:19–23.
De Strooper et al. (1998) "Deficiency of presenilin–1 inhibits the normal cleavage of amyloid precursor protein." *Nature*, vol. 391:387–90.

Evin et al. (1994) "Alzheimer's disease amyloid precursor protein (A PP): proteolytic processing, secretases and A4 amyloid production." *Amyloid: Int. J. Exp. Clin. Invest.*, 1:263–280.
Evin et al. (2000) "Presenilin I expression in yeast lowers secretion of the amyloid precursor protein." *Molecular Neuroscience*, 11(2):405–408.
Faulkner et al. (1987) "pUV I: a new vaccinia virus insertion and expression vector." *Nucleic Acids Research*, 15(17):7192–7193.
Glenner et al. (1989) "Amyloidosis of the nervous system" *Journal of the Neurological Sciences*, 94:1–28.
Goodison et al. (1993) "Neuronal and Glial Gene Expression in Neocortex of Down's Syndrome and Alzheimer's Disease." *Journal of Neuropathology and Experimental Neurology*, 52(3):192–198.
Greenberg et al. (1993) "Anticardiolipin antibodies are an independent risk factor for first ischemic stroke." *Neurology*, 43:2069–2073.
Haan et al. (1990) "Amyloid in central nervous system disease." *Clin. Neurol. Neurosurg.*, 92–4:305–310.
Haan et al. (1994) "Clinical Aspects of Cerebral Amyloid Angiopathy." *Dementia*, 5:210–213.
Haass et al. (1999) "The Presenilins in Alzheimer's Disease—Proteolysis Holds the Key" *Science*, 286:916–919.
Hardy, John (1992) "Framing –amyloid" *Nature Genetics*, 1:233–234.
Hardy, John (1994) "Alzheimer's Disease" *Clinics in Geriatric Medicine*, 10(2):239–247.
Hardy, John (1997) Amyloid, the presenilins and Alzheimer's disease.: *TINS*, 20(4):154–159.
Hartmann, Tobias (1999) "Intracellular biology of Alzheimer's disease amyloid beta peptide." *Psychiatry and Clinical Neuroscience*, 249(6):291–298.
Herreman et al. (1999) "Presenilin 2 deficiency causes mild pulmonary phenotype and no changes in amyloid precursor protein processing but enhances the embryonic lethal phenotype of presenilin 1 deficiency." *PNAS*, 96(21):11872–11877.

(List continued on next page.)

Primary Examiner—John Ulm
Assistant Examiner—Olga N. Chernyshev
(74) Attorney, Agent, or Firm—Karl Bozicevic; Bozicevic, Field & Francis LLP

(57) ABSTRACT

The present invention provides cell-free γ-secretase activity. The method of the invention utilizes a membrane source of APP/γ-secretase mixture in the assay to determine factors that may enhance or decrease enzymatic activity affecting β-amyloid peptide production. The cell membranes used in the assay may be from cells expressing an endogenous APP or, preferably, cells expressing a recombinant APP. The APP may be full-length or a fragment capable of being proteolytically cleaved by γ-secretase. In addition, the APP expressed in the cells may have one or more mutation, such as a point mutation, small deletion, etc.

6 Claims, 5 Drawing Sheets

OTHER PUBLICATIONS

Higgins et al. (1996) "p3 –Amyloid Peptide Has a Unique and Potentially Pathogenic Immunohistochemical Profile in Alzheimer's Disease Brain." *American Journal of Pathology*, 149(2):585–596.

Itoh et al. (1993) "Cerebral amyloid angiopathy: a significant cause of cerebellar as well as lobar cerebral hemorrhage in the ederly." *Journal of the Neurological Sciences*, 116:135–141.

Kang et al. (1987) "The precursor of Alzheimer's disease amyloid A4 protein resembles a cell–surface receptor." *Nature* 325:733–736.

Kitaguchi et al. (1988) "Novel precursor of Alzheimer's disease amyloid protein shows protease inhibitory activity." *Nature*, 331:530–532.

Lannfelt et al. (1994) "Amyloid precursor protein gene mutation at codon 670/671 in familial Alzheimer's disease in Sweden." *Biochem. Soc. Trans.*, 22:176–179.

Levy et al. (1990) "Mutation of the Alzheimer's Disease Amyloid Gene in Hereditary Cerebral Hemorrhage, Dutch Type." *Science*, 248:1124–1126.

Maat–Schieman et al. (1994) "Hereditary cerebral hemorrhage with amyloidosis (Dutch): a model for congophilic plaque formation without neurofibrillary pathology." *Acta Neuropathol.*, 88:371–378.

Masliah et al. (1996) "Comparison of Neurodegenerative Pathology in Transgenic Mice Overexpressing V717F –Amyloid Precursor Protein and Alzheimer's Disease," *J. Neurosci.*, 16:5795–5811.

Octave et al. (2000) "The Role of Presenilin–1 in the –Secretase Cleavage of the Amyloid Precursor Protein of Alzheimer's Disease." *The Journal of Biological Chemistry*, 275(3):1525–1528.

Oyama et al. (1994) "Down's Syndrome: Up–Regulation of –Amyloid Protein Precursor and mRNAs and Their Defective Coordination." *Journal of Neurochemistry*, 62:1062–1066.

Pike et al. (1995) "Structure–Activity Analyses of –Amyloid Peptides: Contributions of the 25–35 Region to Aggregation and Neurotoxicity." *J. Neurochem.*, 64:253–265.

Ponte et al. (1988) "A new A4 amyloid mRNA contains a domain homologous to serine proteinase inhibitors." *Nature*, 331:525–527.

Saftig et al. (1999) "The function of presenilin–1 in amyloid –peptide generation and brain development." *Eur. Arch. Psychiatry Clin. Neurosci.*, 249(6):271–279.

Selkoe et al. (1988) "–Amyloid precursosr protein of Alzheimer disease occurs as 110– to 135–kilodalton membrane–associated proteins in neural and nonneural tissues." *Proc. Natl. Acad. Sci. USA*, 85:7341–7345.

Selkoe, Dennis J. (1996) "Amyloid –Protein and the Genetics of Alzheimer's Disease." *J. Bio. Chem.*, 271(31):18295–18298.

Selkoe, Dennis J. (1999) "Translating cell biology into therapeutic advances in Alzheimer's disease." *Nature*, 399(Supp): A23–A31.

Selkoe, Dennis J. (1993) "Physiological production of the –Amyloid protein and the mechanism of Alzheimer's disease." *Trends Neurosci.*, 16:403–409.

Storey et al. (1999) "The amyloid precursor protein of Alzheimer's disease and the A peptide." *Neuropath. *Appl. Neurol.*, 25:81–97.

Steiner et al. (1999) "Genes and mechanisms involved in –amyloid generation and Alzheimer's disease." *Eur. Arch. Psychiatry Clin. Neurosci.*, 249:266–270.

Tanzi et al. (1988) "Protease inhibitor domain encoded by an amyloid protein precursor mRNA associated with Alzheimer's disease." *Nature*, 331:528–530.

Wattendorff et al. (1995) "Hereditary cerebral haemorrhage with amyloidosis, Dutch type (HCHWA–D): clinicopathological studies." *J. Neurol. Neurosurg. Psychiatry*, 58:699–705.

Wisniewski et al. (1985) "Occurrence of Neuropathological Changes and Dementia of Alzheimer's Disease in Down's Syndrome." *Ann. Neurol.*, 17:278–282.

Wolf et al. (1990) "Identification and characterization of C–terminal fragments of the –amyloid precursor produced in cell culture." *The EMBO Journal*, 9(7):2079–2084.

Wolfe et al. (1999) "Are Presenilins Intramembrane–Cleaving Proteases? Implications for the Molecular Mechanism of Alzheimer's Disease." *Biochemistry*, 38(35):11224–11230.

Wolfe et al. (1999) "Two transmembrane aspartates in presenilin–1 required for presenilin endoproteolysis and –secretase activity." *Nature* 398:513–517.

Yamada et al. (1993) "Subarachnoid haemorrhage in the elderly: a necropsy study of the association with cerebral amyloid angiopathy." *J. Neruol. Neurosurg. Pyschiatry*, 56:543–547.

Ll et al., "Preenilin 1 is linked with $\gamma$–secretase activity in the detergent solubilized state," *PNAS* 97(11):6138–6143 (May 23, 2000).

McClendon et al., "Cell–free assays for $\gamma$–secretase activity," *The FASFB Journal* 14:2383–2386 (Dec. 2000).

Dorothy I. Mundy, "Identification of the Multicatalytic Enzyme as a Possible $\gamma$–secretase for the Amyloid Precursor Protein," *Biochem Biophys Res. Comm.* 204(1):333–341 (Oct. 14, 1994).

Pinnix et al., "A Novel $\gamma$–Secretase Assay Based on Detection of the Putative C–terminal Fragment–$\gamma$ of Amyloid $\beta$ Protein Precursor," *J. Biol. Chem.*, 276(1):481–487 (Jan. 5, 2001).

Shoji et al., "Production of the Alzheimer Amyloid $\beta$ Protein by Normal Proteolytic Processing," *Science* 258:126–129 (Oct. 2, 1992).

Shpungin et al., "Activation of the Superoxide Forming NADPH Oxidase in a Cell–free System by Sodium Dodecyl Sulfate," *J. Biol. Chem.* 264(16):9195–9203 (Jun. 5, 1989).

* cited by examiner ns.
MODULATION OF γ-SECRETASE ACTIVITY

CROSS-REFERENCE

This application claims priority to, and incorporates by reference in its entirety, earlier filed provisional Patent Application 60/203,506 filed May 11, 2000.

FIELD OF THE INVENTION

The invention relates to proteolytic processing of the β-amyloid precursor protein, and more particularly to assays for determining factors that affect such processing.

BACKGROUND OF THE INVENTION

A number of important neurological diseases including Alzheimer's disease (AD), cerebral amyloid angiopathy (CAA), and prion-mediated diseases are characterized by the deposition of aggregated proteins, referred to as amyloid, in the central nervous system (CNS) (for reviews, see Glenner et al. (1989) *J Neurol. Sci.* 94:1–28; Haan et al. (1990) *Clin. Neurol. Neurosurg.* 92(4):305–310. These highly insoluble aggregates are composed of nonbranching, fibrillar proteins with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) *Neuroreport* 6:477–80; Masliah et al. (1996) *J. Neurosci.* 16:5795–5811). AD studies additionally indicate that amyloid fibrils may actually initiate neurodegeneration (Lendon et al. (1997) *J. Am. Med. Assoc.* 277:825–31; Yankner (1996) *Nat. Med.* 2:850–2; Selkoe (1996) *J. Biol. Chem.* 271:18295–8; Hardy (1997) *Trends Neurosci.* 20:154–9).

AD and CAA share biochemical and neuropathological markers, but differ somewhat in the extent and location of amyloid deposits as well as in the symptoms exhibited by affected individuals. The neurodegenerative process of AD, the most common cause of progressive intellectual failure in aged humans, is characterized by the progressive and irreversible deafferentation of the limbic system, association neocortex, and basal forebrain accompanied by neuritic plaque and tangle formation (for a review see Terry et al. (1994) "Structural alteration in Alzheimer's disease." In: Alzheimer's disease (Terry et al. eds.), pp. 179–196. Raven Press, New York). Dystrophic neurites, as well as reactive astrocytes and microglia, are associated with these amyloid-associated neurite plaques. Although, the neuritic population in any given plaque is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy (1997) *Trends Neurosci.* 20:154–9; Haan et al. (1990) *Clin. Neurol. Neurosurg.* 92:305–10; Terry et al., supra; Vinters (1987) *Stroke* 18:211–24; Itoh et al. (1993) *J. Neurological Sci.* 1 16:135–41; Yamada et al. (1993) *J Neurol. Neurosurg. Psychiatry* 56:543–7; Greenberg et al. (1993) *Neurology* 43:2073–9; Levy et al. (1990) *Science* 248:1124–6). In some familial CAA cases, dementia was noted before the onset of hemorrhages, suggesting the possibility that cerebrovascular amyloid deposits may also interfere with cognitive functions.

In both AD and CAA, the main amyloid component is the amyloid protein (Aβ). The Aβ peptide, which is generated from the amyloid precursor protein (APP) by two putative secretases, is present at low levels in the normal CNS and blood. Two major variants, $A\beta_{1-40}$ and $A\beta_{1-42}$, are produced by alternative carboxy-terminal truncation of APP (Selkoe et al.(1988) *Proc. Natl. Acad. Sci. USA* 85:7341–7345; Selkoe, (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

The formation of Aβ is considered to be a key pathogenic process in Alzheimer's disease and related neurodegenerative disorders (reviewed by Selkoe in Nature Suppl.399: A23, 1999). The precise mechanisms by which neuritic plaques are formed and the relationship of plaque formation to the AD-associated, and CAA-associated neurodegenerative processes are not well-defined. However, evidence indicates that dysregulated expression and/or processing of APP gene products or derivatives of these gene products derivatives are involved in the pathophysiological process leading to neurodegeneration and plaque formation. For example, missense mutations in APP are tightly linked to autosomal dominant forms of AD (Hardy (1994) *Clin. Geriatr. Med.* 10:239–247; Mann et al. (1992) *Neurodegeneration* 1:201–215). The role of APP in neurodegenerative disease is further implicated by the observation that persons with Down's syndrome who carry an additional copy of the human APP (hAPP) gene on their third chromosome 21 show an overexpression of hAPP (Goodison et al. (1993) *J. Neuropathol. Exp. Neurol.* 52:192–198; Oyama et al. (1994) *J. Neurochem.* 62:1062–1066) as well as a prominent tendency to develop AD-type pathology early in life (Wisniewski et al. (1985) *Ann. Neurol.* 17:278–282). Mutations in Aβ are linked to CAA associated with hereditary cerebral hemorrhage with amyloidosis (Dutch (HCHWA-D) (Levy et al. (1990), supra), in which amyloid deposits preferentially occur in the cerebrovascular wall with some occurrence of diffuse plaques (Maat-Schieman et al. (1994) *Acta Neuropathol.* 88:371–8; Wattendorff et al. (1995) *J. Neurol. Neurosurg. Psychiatry* 58:699–705). A number of hAPP point mutations that are tightly associated with the development of familial AD encode amino acid changes close to either side of the Aβ peptide (for a review, see, e.g., Lannfelt et al. (1994) *Biochem. Soc Trans.* 22:176–179; Clark et al. (1993) *Arch. Neurol.* 50:1164–1172). Finally, in vitro studies indicate that aggregated Aβ can induce neurodegeneration (see, e.g., Pike et al. (1995) *J. Neurochem.* 64:253–265).

APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) *Nature* 325:733–736, which is designated as the "normal" APP. A 751-amino acid polypeptide has been described by Ponte et al. (1988) Nature 331:525–527 and Tanzi et al. (1988) Nature 331:528–530. A 770-amino acid isotype of APP is described in Kitaguchi et al. (1988) Nature 331 :530–532. A number of specific variants of APP have also been described having point mutations which can differ in both position and phenotype. A general review of such mutations is provided in Hardy (1992) Nature Genet. 1:233–234. A mutation of particular interest is designated the "Swedish" mutation where the normal Lys-Met residues at positions 595 and 596 are replaced by Asn-Leu. This mutation is located directly upstream of the normal β-secretase cleavage site of APP, which occurs between residues 596 and 597 of the 695 isotype.

APP is post-translationally processed by several proteolytic pathways resulting in the secretion of various fragments or intracellular fragmentation and degradation. F. Checler, *J. Neurochem.* 65:1431–1444 (1995). The combined activity of β-secretase and γ-secretase on APP releases an intact β-amyloid peptide (Aβ), which is a major constituent of amyloid plaques. Aβ is an approximately 43 amino acid peptide which comprises residues 597–640 of the 695 amino acid isotype of APP. Internal cleavage of APP by α-secretase inhibits the release of the full-length Aβ peptide. Although the extent of pathogenic involvement of the secretases in AD progression is not fully elucidated, these proteolytic events are known to either promote or inhibit Aβ formation, and thus are thought to be good therapeutic candidates for AD.

Although a number of assays have been developed to examine secretase activity, each of these has limitations. Available cell-free assays which typically utilize synthetic substrates are not entirely reflective of the in vivo situation. Also, conditions of preparation and performing the cell-free assays have not been designed to reflect the in vivo state. Whole cell assays, although they accurately reflect physiological states of enzyme activity, are more difficult because the agents affecting enzymatic activity must be permeable to the cell as well as the subcellular compartments.

Numerous reports have been made describing the isolation and identification of putative γ-secretases (reviewed by Evin et al. in Amyloid 1: 263, 1994). It has been proposed that PS1 is γ-secretase (Wolfe et al. Nature 398: 513, 1999). The evidence supporting this proposal is indirect but has nonetheless prompted considerable discussion (Wolfe et al. Biochem. 38: 11223, 1999; Annaert & De Strooper TINS 22: 439, 1999). However, none of these putative γ-secretases has been definitively proven to be the authentic activity capable of producing Aβ. The ability to produce Aβ in vitro using a solubilized mammalian cell extract allows for purification and definitive identification of γ-secretase activity. Moreover, this assay has the advantage that (1) it uses the native substrate derived from β-amyloid precursor protein, APP, and not synthetic or chimeric APP substrates and (2) the γ-secretase activity is monitored by following the production of authentic Aβ protein. In addition, two major Aβ isoforms are generated by γ-secretase action, $A\beta_{40}$ and $A\beta_{42}$, representing 40 and 42 amino acid long proteins, respectively. It has been debated whether a single enzymatic activity is responsible for the generation of all Aβ isoforms or whether distinct γ-secretases exist, one generating each Aβ isoform. With this solubilized system for γ-secretase activity this issue can be resolved. The generation of specific Aβ isoforms can be assessed and the enzymatic activity for each purified, if multiple activities exist. If only one enzyme produces the Aβ isoforms, this will be apparent in the purification process. Knowledge of single versus multiple γ-secretases is important with regard to development of inhibitors of γ-secretase and Aβ formation. In particular, it may be advantageous to selectively inhibit $A\beta_{42}$ as this has been shown to be more pathogenic by a number of criteria (reviewed by Selkoe in J. Biol. Chem. 271: 18295, 1996; Sotrey & Cappai in Neuropath. & Appl. Neurol. 25: 81, 1999). Furthermore, because the γ-secretase cleavage site on APP appears to be located in the transmembrane domain, the role of lipids or a membrane-like milieu can also be assessed with this assay system.

It is evident from a number of reports that presenilin proteins (PS1 & PS2) are involved in γ-secretase processing of Aβ. For example, cells from PS1 knock out mice display a reduced level of Aβ protein and a concomitant increase in the immediate precursor to Aβ, the carboxyl-terminal 99 residue domain of APP (De Strooper et al. Nature 391: 387, 1998). PS2 knock out mice do not appear to significantly influence γ-secretase processing to Aβ (Herreman et al. Proc. Natl. Acad. Sci. USA 96: 11872, 1999) although other reports suggest a role for PS2 in Aβ formation (Jacobsen et al. J. Biol. Chem. 274: 35233, 1999; Steiner et al. J. Biol. Chem. 274: 28669, 1999). More recent evidence in fact suggests that PS1, although necessary for γ-secretase activity, is not in fact γ-secretase (Octave et al., J. Biol. Chem 275: 1525–1528).

There is thus a need in the art for a system to identify the molecules responsible for γ-secretase activity. There is also a need for an efficient and reproducible method of identifying inhibitors/modulators of γ-secretase activity that affect APP processing. There is especially a need for an assay that more accurately reflects in vivo activity of this enzymatic activity.

SUMMARY OF THE INVENTION

The present invention provides a solubilized γ-secretase system and a cell-free assay for identifying modulators of the APP processing enzyme γ-secretase. The method of the invention utilizes either a membrane source of both APP and γ-secretase or individual membrane sources for APP and secretase to provide a solubilized γ-secretase activity and to determine factors that may enhance or decrease enzymatic activity affecting Aβ peptide production. The cell membranes used in the assay may be from cells expressing an endogenous APP or, preferably, cells expressing a recombinant human APP. The APP may be full-length or a fragment capable of being proteolytically cleaved by γ-secretase, e.g., CT99. In addition, the APP expressed in the cells may have one or more mutation, such as a point mutation, small deletion, etc.

In one embodiment, the invention provides a method for producing solubilized γ-secretase activity. The isolated solubilized γ-secretase activity can be used for a variety of purposes including the generation of Aβ and the identification and isolation of molecules(s) responsible for the γ-secretase activity. Identification and characterization of the molecules responsible for γ-secretase activity will allow the rational design of inhibitors which act directly on γ-secretase to prevent Aβ formation. The solubilized γ-secretase activity can be isolated with APP or an APP proteolytic product, or it may be reconstituted as a mixture between isolated γ-secretase activity and APP or an APP proteolytic product.

In another embodiment, crude membrane preparations having γ-secretase activity are provided. These membrane preparations are composed of at least the γ-secretase activity, but may also have numerous other membrane-bound cellular products. These membrane preparations are particularly useful in determining the potential effect of agents that affect γ-secretase activity on other membrane molecules.

In yet another embodiment, the invention provides an assay for identifying compounds which modulate γ-secretase activity. The assay method of the invention includes the steps of 1) obtaining cell membranes from cells expressing endogenous and/or exogenous APP or an APP proteolytic product (e.g., recombinant APP), 2) removing background γ-secretase products of APP (e.g., Aβ, p3 and/or γCTF) present in the cells at the time of preparation; 3) incubating the membrane preparations with an agent that potentially modifies γ-secretase activity; and 4) detecting the proteolytic products of γ-secretase, e.g., γCTF, p3 and/or Aβ. Detection may be accomplished using an antibody that selectively recognizes the γ-secretase products, or by other methods such as isolation and characterization of the γ-secretase products. The present assays can detect very small increases in proteolytic product, with an assay being sensitive within a range of 0.5 to 4 ng/ml product for an ELISA assay and within a range of 0.002–0.05 ng/ml using Western Blot analysis of the product.

In a particular embodiment, the membranes used for isolation of γ-secretase activity are obtained from cells that express a gene altered from a normal, endogenous gene. For example, the cells may express an APP altered to be more or less vulnerable to secretase activity, e.g. mutations to increase γ-secretase cleavage. In another example, other genes involved in γ-secretase activity, such as the presenilins, may be altered to identify agents that can compensate for these mutations. Specifically, mutations known to occur in the population can be used to identify agents that are particularly useful in the treatment of subjects having such mutations.

In another embodiment, the assay utilizes an agent that increases γ-secretase activity, e.g. cardiolipin or other phospholipids, to increase the sensitivity of the assay.

An object of the invention is to identify therapeutic agents that inhibit the activity of γ-secretase, thus inhibiting production of Aβ, and more specifically $A\beta_{42}$. Such agents are useful to prevent formation of neuritic plaques in subjects in need of such, for example subjects at risk for familial AD.

Yet another object of the invention is the method of isolation of complexes or components comprised of an agent and the molecules involved in γ-secretase activity. This can be used to identify the specific molecules involved in γ-secretase activity as well as the specific mutations of these molecules. Isolation of these complexes can be accomplished via techniques such as co-immunoprecipitation.

One advantage of the assay of the invention is that it more authentically reflects in vivo changes in γ-secretase activity with the native APP substrate compared to other assays using peptide or semi-synthetic substrates. The membranes are also solubilized which aids in the ease of performing the assay and in reconstitution and purification of γ-secretase activity.

Another advantage of the assay of the invention is that it allows efficient delivery of potential agents affecting γ-secretase activity interaction with the natural enzyme without the problems of whole cell assays or microsomal assays, e.g. penetration of the agent across the cell membrane Yet another advantage is that the γ-secretase-agent complexes produced in the assay of the invention may be more easily purified than the γ-secretases themselves, and thus the assay may be useful to determine the actual molecules involved in the proteolysis and/or secretion of the proteolytic products.

Yet another advantage of the assay of the invention is that γ-secretase activity is determined by a direct measurement of γ-secretase proteolytic products.

Yet another advantage of the assay of the invention is that components, such as phospholipids, can be added which enhance the γ-secretase activity and/or stabilize γ-secretase products, e.g., Aβ, p3 and/or γCTF.

Yet another advantage of the assay of the invention is that the assay is cell-free, and yet does not rely on one subcellular organelle as do other assays such as microsomal assays. The described assays are thus more reflective of the γ-secretase activity in all parts of the cell, including the endoplasmic reticulum, the golgi, etc.

These and other objects, advantages, and features of the invention will become apparent to those persons skilled in the art upon reading the details of the invention as more fully described below.

DETAILED DESCRIPTION OF PREFERRED EMBODIMENTS

Figure 1:
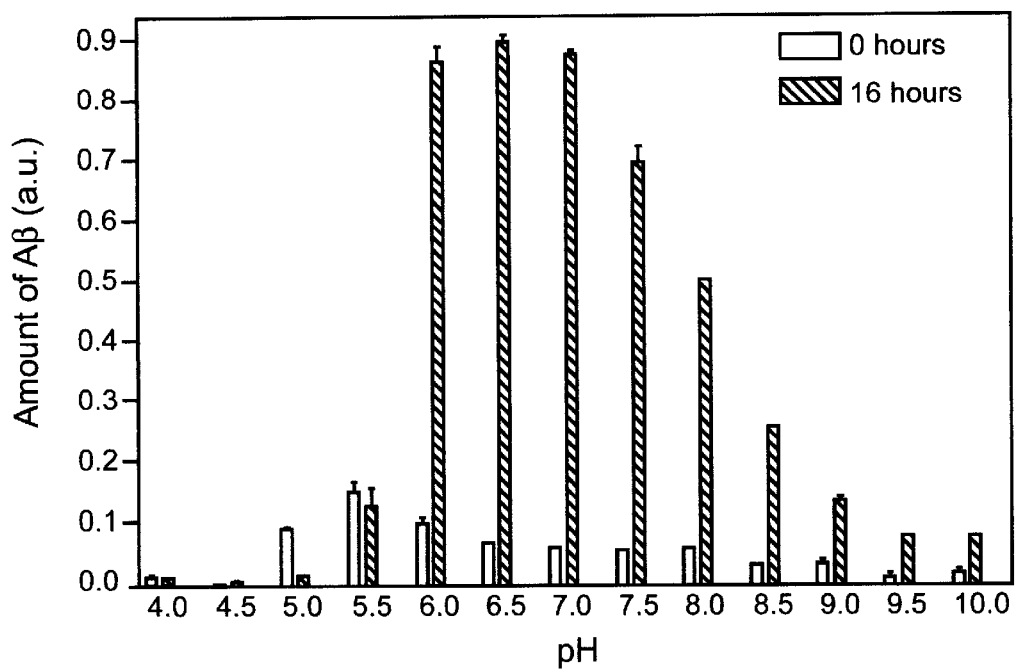
FIG. 1 is a bar graph illustrating the effect of pH on γ-secretase activity present in the membrane extract.

Before the present assays are described, it is to be understood that this invention is not limited to particular methodology described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

As used herein, "β-amyloid precursor protein" (APP) refers to a polypeptide that is encoded by a gene of the same name localized in humans on the long arm of chromosome 21 and that includes a β-amyloid protein region within its carboxyl region.

The term "β-amyloid protein" (AβD) as used herein refers to all β-amyloid proteins including approximately 43 amino acid peptide which comprises residues 597–640 of the 695 amino acid isotype of APP, residues 653–696 of the 751 isotype, and residues 662–705 of the 770 isotype. As described herein, the protein will be referred to using the 695 numbering system. The Ad proteins of the invention include any protein containing about 40 to about 44 amino acids which preferably comprises residues 597–640 of the 695 amino acid isotype APP, $A\beta_{1-40}$ or $A\beta_{1-42}$ (Selkoe et al., supra). Within this disclosure the term Aβ protein is intended to include the two major Aβ variants referred to herein and the 55 amino acid segments including amino acids 640–695 of the 695 amino acids isotype of APP. After this disclosure others will, perhaps, discover other β-amyloid proteins and as such they are intended to come within the scope of the present invention.

The term "APP secretase", "secretase" and "secretase activity" as used interchangeably herein refers to any proteolytic enzyme and/or activity which results in the secretion of various fragments or intracellular fragmentation and degradation of APP.

This includes α-secretase, β-secretase, γ-secretase, and any similar but as of yet unidentified enzymes which cause the proteolysis of either APP or APP proteolytic products such as CT99.

The term "γ-secretase" and "γ-secretase activity" as used interchangeably herein refers to the enzyme or enzymes responsible for proteolysis of APP or an APP proteolytic product (e.g. a C-terminal fragment of APP that contains the entire Aβ sequence) at the intramembrane C-terminal cleavage site of APP, which results in the products $A\beta_{40}$ or $A\beta_{42}$, or longer or shorter Aβ forms, e.g., $A\beta_{44}$ and $A\beta_{38}$.

The term "APP/γ-secretase mixture" as.used herein refers to the isolated APP and γ-secretase as a complex and/or as a mixture of the two substances. This term is intended to cover mixtures having γ-secretase combined with full-length APP as well as γ-secretase combined with proteolytic products of APP such as CT99and CT83, and recombinant products such as CT100. The term can also refer to APP/γ-secretase mixtures containing presenilin 1 or presenilin 2 proteins.

The term "CT99" as used herein refers to the APP proteolytic product produced by proteolytic processing of APP with β-secretase. The term "CT100" as used herein refers to a recombinant protein product having all of the residues of CT99 following an initial methionine codon. Both of these products are substrates for γ-secretase, and can be used in the assays of the invention to detect γ-secretase activity. CT99 is the true, native substrate for γ-secretase.

The term "APP proteolytic product" as used herein refers to each of the potential products that can be obtained using the APP secretases, including: CT99 or CT100, which are products of β-secretase, and which may be used as a substrate to detect γ-secretase activity; p3, which is a product of (α-secretase and γ-secretase; Aβ, which is a product of β-secretase and γ-secretase; and γCTF, which is the carboxy terminal product of γ-secretase. Preferably, the present invention measures γ-secretase activity through detection of a γ-secretase product, such as p3, Aβ and γCTF.

The term "Alzheimer's disease" (abbreviated herein as "AD") as used herein refers to a condition associated with formation of neuritic plaques comprising ,β-amyloid protein primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing β-amyloid protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics. The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" and "Aβ deposit" as used interchageably herein refer to a deposit in the brain composed of Aβ as well as other substances.

By "antibody" is meant an immunoglobulin protein which is capable of binding an antigen. Antibody as used herein is meant to include the entire antibody as well as any antibody fragments (e.g. F(ab')$_2$, Fab', Fab, Fv) capable of binding the epitope, antigen or antigenic fragment of interest.

Antibodies of the invention are immunoreactive or immunospecific for and therefore specifically and selectively bind specific proteolytic products of the APP protein, and in particular products generated by γ-secretase activity. Antibodies for each proteolytic product are preferably immunospecific—i.e., not substantially cross-reactive with other proteolytic products of APP. Although the term "antibody" encompasses all types of antibodies both polyclonal and monoclonal antibodies, and produced using a peptide antigen.

By "purified antibody" is meant one which is sufficiently free of other proteins, carbohydrates, and lipids with which it is naturally associated. Such an antibody "preferentially binds" to a proteolytic APP protein product (or an antigenic fragment thereof), i.e., does not substantially recognize and bind to other antigenically-unrelated molecules. A purified antibody of the invention is preferably immunoreactive with and immunospecific for a particular APP protein product (e.g. γCTF) and more preferably will not react with other APP protein products.

By "antigenic fragment" of an APP proteolytic product is meant a portion of such a protein which is capable of binding an antibody used in the assay of the invention.

By "binds specifically"

is meant high avidity and/or high affinity binding of an antibody to a specific polypeptide i.e., epitope of a APP protein product. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to APP protein product than other epitopes so that by adjusting binding conditions the antibody binds almost exclusively to the APP protein product. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention bind to a particular APP protein product with a binding affinity of $10^7$ $M^{-1}$ or more, preferably $10^8$ mole/liters or more. In general, an antibody with a binding affinity of $10^6$ $M^{-1}$ or less is not useful in that it will not bind an antigen at a detectable level using conventional methodology currently used.

By "detectably labeled antibody" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

The term "compound" as used herein describes any molecule, e.g. protein, naturally occurring substances, synthesized protein or small molecule pharmaceutical, with the capability of affecting secretase activity. Such compounds may be used to treat the molecular and clinical phenomena associated with amyloid-associated disorders, and specifically AD, CAA, and prion-mediated disorder.

By "effective dose" or "amount effective" is meant an administration of a compound sufficient to provide the desired physiological and/or psychological change.

This will vary depending on the patient, the disease and the treatment. The dose may either be a therapeutic dose, in which case it should sufficiently alter levels of amyloid plaques in the subject to alleviate or ameliorate the symptoms of the disorder or condition, or a prophylactic dose, which should be sufficient to prevent accumulation of amyloid plaques to an undesirable level.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease and/or ameliorating the symptoms. The therapeutic agents that can be identified using the assay of the invention are particularly useful in the treatment of any disease associated with the deposition of β-amyloid, including AD, hereditary cerebral hemorrhage with amyloidosis, and prion-mediated disorders, and the like.

GENERAL ASPECTS OF THE INVENTION

The present invention provides a preparation of either membranes containing γ-secretase or solubilized γ-secretase activity that maintains the ability to enzymatically process APP in vitro. The γ-secretase activity is isolated as a mixture with APP or an APP proteolytic product, thus maintaining the integrity of the proteins responsible for γ-secretase activity. Alternatively, the γ-secretase activity can be isolated and reconstituted with APP or an APP proteolytic product. The APP/γ-secretase mixture can be used directly to assess the level of production of Aβ in response to various genetic backgrounds and/or added compounds. The APP/γ-secretase mixture can also be incubated with exogenous APP to produce high levels of Aβ for various uses, such as in vitro studies of plaque formation and isoform specific antibody production. The ability to reconstitute γ-secretase activity with its natural substrate to generate Aβ protein in vitro has heretofore not been achieved.

The solubilized γ-secretase preparations can also be used to identify the molecule(s) responsible for γ-secretase processing of APP. Specifically, the present invention will allow the clarification of the role of PS1 and PS2 in the generation of Aβ. PS1 and PS2 proteins can be removed from the solubilized preparation or PS1 or PS2 null cells can be used to prepare the solubilized γ-secretase activity, after which the preparation can be tested for Aβ production. Alternatively, the preparations can be treated with a compound that binds to γ-secretase, and γ-secretase identified via isolation of the γ-secretase/compound complex.

The solubilized γ-secretase activity provides an assay for detecting γ-secretase processing of APP in a cell-free assay. The γ-secretase activity can be reconstituted with isolated APP or APP proteolytic products produced from membranes and the activity determined by measuring levels of the proteolytic products of APP, i.e. $A\beta_{40}$ and $A\beta_{42}$. This assay system has advantages over more common approaches used to identify Aβ inhibitors which involve intact cells or microsomes. The present assay allows the testing of the effect of different compounds on APP processing without limitations found in conventional whole cell or cell-free (e.g. microsomal) assays. For example, the solubilized preparations of the assay of the invention allow a compound access to molecules involved in processing without the issues of transport across a membrane. The assay using the solubilized γ-secretase can have a much higher concentration of activity of interest than a whole cell preparation, since the percentage of γ-secretase is much higher, thus allowing the identification of more subtle effects on APP processing.

Moreover, with an intact cell approach, the specific target and/or mechanism by which Aβ inhibitors are acting is unknown or surmised. This assay offers the ability to identify and separate specific targets involved in the formation of the carboxyl-terminus of Aβ. The development of Aβ inhibitors would be greatly facilitated by having isolated γ-secretase in a semi-purified or purified state, along with other components identified as critical.

PREPARATION OF SOLUBILIZED γ-SECRETASE ACTIVITY

The cell-free γ-secretase activity of the invention can be produced using a variety of mammalian cells since essentially all mammalian cells examined have been shown to generate Aβ protein. The cells used to obtain the membrane preparation can be any cells of interest, e.g. primary glial cells, mammalian cells expressing endogenous or exogenous human APP, human 293 cells, and the like. Cells transiently or stably expressing APP, as well as non-transformed cells, can be used to produce the active γ-secretase extract. Transfected cells can be placed under drug selection so that a stable line expressing high levels of APP or an APP product can be isolated. Typically, the commercially available expression plasmids harbor selectable drug markers suitable for mammalian cells.

The cells used to isolate the γ-secretase activity can be modified to express certain proteins or isoforms of proteins that may affect the proteolysis of APP by γ-secretase and/or enhance the efficacy of the assay. For example, cells having specific mutations in APP can be used to determine the effect these mutations may have on the ability of γ-secretase proteolysis. The "Swedish" mutation of APP (K595N/M596L) which increases γ-secretase processing is a naturally occurring mutation which can be applied to this assay. Other point mutations near the γ-secretase cleavage site associated with increased $A\beta_{42}$ production can also be used.

In another example, cells having mutations in a presenilin gene, and in particular presenilin 1, may be used to isolate the γ-secretase activity to examine the effect this has on γ-secretase activity. This can be used to determine whether or not presenilins are in fact responsible for γ-secretase activity.

In yet another example, cells transiently or stably expressing the β-secretase product of APP, the immediate precursor of AP, can be used in the isolation of the γ-secretase activity. The immediate precursor of Aβ is comprised of the carboxyl-terminal 99 amino acids of APP, which is referred to as CT99. The CT99 portion of APP contains the transmembrane domain and is, therefore, membrane associated. CT99 can be engineered so that it is expressed at high levels in mammalian cells which increases the levels of Aβ generated by the cell-free assay. For example, an expression construct can be made using vectors such as pCDNA3.1 (InVitrogen) which utilizes the cytomegalovirus promoter to drive expression of the inserted sequence. Since the CT99 sequence is naturally preceded by a methionine residue, this can serve as an initiator codon. Hence, one can use basic cloning methods to introduce CT100 (CT99 plus the preceding methionine) into an expression plasmid. Once the recombinant plasmid is constructed and verified, it can be introduced into mammalian cells using a variety of techniques such as Lipofectamine Plus (Gibco BRL) or calcium phosphate precipitation. The transfected cells can be harvested 24–72 hours post introduction of the DNA at a time determined to yield optimal levels of CT100.

The APP/γ-secretase complex is prepared from cell membranes to allow access of the endogenous or exogenous APP protein with γ-secretase activity. Membrane preparations used in the assay of the invention can be homogenized using techniques available to those skilled in the art, such as douncing, use of a mechanical tissue homogenizer, needle shearing, and use of a ball-bearing tissue homogenizer. Generally, cells are isolated and disrupted in a manner to preserve the γ-secretase activity. The cells used for the membrane preparation may be freshly obtained, e.g. isolated from a patient sample, from a cultured system, e.g. an immortal cell line, or cells present in long-term storage, e.g. cells stored at −70 C. Once the membranes have been isolated, they may be used directly in the assay or stored for future use, e.g. at −80 C.

Once a crude cell membrane preparation has been generated, the membranes are optionally treated to remove the background APP proteolytic products and non-specific proteolytic activity that degrades Aβ. For example, the preparations may be treated with a mild detergent to remove background levels of APP γ-secretase proteolytic products. An exemplary detergent for use with the presently described assay include 0.02–0.05% saponin. Following this initial treatment, the pelleted membranes are solubilized with a stronger detergent, preferably with 0.5% CHAPS.

Once solubilized, the APP/γ-secretase mixture is optionally partially purified.

The mixture can be purified using any method known in the art, but preferably are purified using chromatography, e.g. HiTrap Q chromatography. Other techniques that may be used include, but are not limited to, ion exchange chromatographies such as DEAE; size exclusion chromatography; HPLC, such as reverse phase HPLC; and other methods that will be apparent to one skilled in the art upon reading the present disclosure.

Optionally, before use, the APP/γ-secretase mixture is exposed to an agent that alters γ-secretase activity and/or stabilizes the detectable APP proteolytic products of γ-secretase. In a preferred embodiment, the agent enhances the level of γ-secretase activity in order to allow for improved detection of alterations in γ-secretase activity. Exemplary agents for this use include cardiolipin and alpha-phospholipids such as L-alpha-phosphatidylserine and L-alpha-phosphotidylcholine. Other agents affecting γ-secretase activity can be used in the present invention as well, as will be obvious to one skilled in the art upon reading this disclosure.

ASSAY METHODOLOGY

The present invention provides an assay methodology for determining compounds which can have an effect, and preferably which reduce, APP proteolytic products using membrane-enzyme mixtures. Such compounds can be used in the treatment of patients, particularly humans, with amyloid-associated disorders. The assay involves contacting APP/γ-secretase as individual components or as a mixture with a test compound and thereafter determining the level of APP proteolytic products, and particularly γCTF and Aβ. If the compound reduces the level of APP proteolytic products, e.g. as compared with a previously known standard then the compound is a candidate for the treatment for patients with amyloid-associated disorders. The APP and γ-secretase which are contacted with the compound can be associated with cell membranes, or isolated with membranes as a mixture obtained from cells expressing APP and γ-secretase and reconstituted. Although different types of cells can be used it is preferable to use cells which have been recombinantly modified to express APP as a source of substrate for γ-secretase.

In one aspect of the invention there is a disclosed method of identifying a compound characterized by its ability to alter γ-secretase activity. An assay method for determining compounds that affect APP γ-secretase activity is disclosed which comprises: (1) preparation of APP and γ-secretase present on or derived from cell membranes prepared from cells expressing APP and γ-secretase; (2) treatment of the APP plus γ-secretase with a candidate compound in vitro; and (3) determining the effect of the compound on γ-secretase activity by measuring the levels of APP proteolytic products. It is preferable to run the assay against a control, e.g., where no compound is added to the APP/γ-secretase mixture and/or where any carrier added with the test compound is added to a culture to determine if a carrier alone effects APP proteolysis.

Before use of the solubilized γ-secretase activity in the assay, background levels of APP proteolytic products are preferably removed, e.g. by treatment with detergent. Alternatively, this step can be eliminated by precisely determining the level of APP proteolytic products in a known cell culture of cells expressing APP. Thereafter the known level could be adjusted for in the assay, i.e. increases or decreases relative to the known background level could be determined by subtracting away the known background level. In order to perform the assay in this manner, it would, of course, be necessary to obtain cell membranes from a statistically significant number of recombinant cells which express a known level of APP and thereafter determining the background level of APP proteolytic products present in the membranes of these cells.

Novel methods are provided which employ compounds that are effective in altering γ-secretase activity levels. Compounds found to inhibit or enhance γ-secretase activity can be further assayed in transgenic mice to determine additional physiological effects and potential of the compound as a therapeutic agent. Compounds which test positive for inhibition can be used in a specific method of treatment of the invention described below.

Candidate Compounds for Use with the Assays of the Invention

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

Compounds for use in the method of the invention may be small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including, but not limited to: peptides, saccharides, fatty acids, steroids, purines, pyrimidines, derivatives, structural analogs or combinations thereof.

Detection of Proteolytic Products Following Treatment of APP/γ-Secretase Mixture Following incubation of the APP/γ-secretase mixture with the test compound, the preparation is assayed for levels of γ-secretase proteolytic products of APP, e.g. γCTF, p3 and/or Aβ. Detection of the APP/γ-secretase proteolytic products can be accomplished using any of a number of methods to determine the absence or presence or altered amounts of the differentially expressed polypeptide in the test sample. For example, detection can utilize staining of the APP/γ-secretase mixture with labeled antibodies, performed in accordance with conventional methods. In general, antibodies that specifically bind a differentially expressed polypeptide of the invention are added to a sample, and incubated for a period of time sufficient to allow binding to the epitope, usually 30 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, colorimetric assay etc. Any suitable alternative methods of qualitative or quantitative detection of levels or amounts of differentially expressed polypeptide can be used, for example western blot, immunoprecipitation, radioimmunoassay, etc.

In a preferred embodiment, an enzyme-linked immunosorbent assay (ELISA) assay is used to detect the presence of the APP γ-secretase proteolytic product, γCTF, p3 and/or Aβ. Quantitation of multiple samples can be made more time efficient by running the assay in an ELISA format in which different potential agents are tested against cell membrane preparations and rapid quantitation is accomplished by spectrophotometric or colorimetric detection. For example, the presence of a relatively low amount of γCTF or Aβ indicates a decrease in γ-secretase activity. Such changes in the level of APP proteolytic peptide products can identify lead compounds for further study in the treatment of amyloid-associated disorders. Compounds found to affect γ-secretase activity, e.g. either inhibit or enhance secretase activity, can be further assayed in transgenic mice. Compounds which test positive in the assay of the invention can be used in the described treatment of amyloid-associated disorders such as AD and CAA.

Methods of Treament Using Compounds of the Invention

The method of treatment is a method of reducing the level of β-amyloid plaque in the brain tissue of a mammalian host by administering a compound which showed positive results in the assay described above. In general, such compounds will reduce the level of β-amyloid plaque in brain tissue by affecting in vivo levels of γ-secretase. Therapeutic effects may be seen, for example, by compounds that inhibit or decrease γ-secretase activity. Prophylactic use is also contemplated for individuals at risk for Alzheimer's disease such as the elderly and/or individuals carrying known mutations linked to this disorder. Individuals treated may not presently exhibit symptoms but have been subjected to head and neuronal trauma.

In the subject methods, the compound may be administered to the host using any convenient means capable of resulting in the desired target protein activity modulation. Thus, the compound can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, transdermal patches, suppositories, injections, inhalants and aerosols.

As such, administration of the compounds can be achieved in various ways, including oral, buccal, rectal, parenteral, intraperitoneal, intravaginal, intradermal, transdermal, intratracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules. Examples of additives are conventional additives, such as lactose, mannitol, corn starch or potato starch; binders, such as crystalline cellulose, cellulose derivatives, acacia, corn starch or gelatins; disintegrators, such as corn starch, potato starch or sodium carboxymethylcellulose; lubricants, such as talc or magnesium stearate; and if desired, diluents, buffering agents, moistening agents, preservatives and flavoring agents.

The compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol. If desired, conventional additives such as solubilizers, isotonic agents, suspending agents, emulsifying agents, stabilizers and preservatives may also be added. The concentration of therapeutically active compound in the formulation may vary from about 0.5–100 wt. %.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit (e.g., a teaspoonful, tablespoonful, tablet or suppository) contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compounds are added to a host in a physiologically acceptable carrier, at a dosage from 5 mg to 1400 mg, more usually from 100 mg to 1000 mg, preferably 500 to 700 for a dose of 0.5 to 20 mg/kg weight. The dosage for compounds altering secretase activity is elected so that the secretase activity is altered by 10 to 80%, more preferably 20 to 70% and even more preferably 25–50%.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1.

Preparation of a Mammalian Cell-Free γ-secretase System.

A γ-secretase preparation was produced from cells expressing the C-terminal cleavage product of APP. A recombinant vaccinia virus was constructed from the human βAPP751 cDNA and found to produce high levels of CT99 (Wolf et al. EMBO J. 9: 2079, 1990). This recombinant virus, referred to as VV99, was constructed as follows. First, the carboxyl-terminal 1 kb of the βPP gene was digested with DdeI and PvuII, and a 590 bp fragment was isolated using gel electrophoresis and subsequent gel purification. A 27 bp EcoRI-DdeI adaptor sequence was cloned into the EcoRI-SmaI digested vaccinia virus vector, pUV1 (Falkner et al. Nuc. Acids Res. 15: 7192, 1987). The 27 bp adaptor altered the coding region of the viral sequences such that the first amino acid of the βAPP sequence expressed from the viral plasmid corresponded to the aspartate at position 653, i.e., the first amino acid of Aβ. The initiator methionine was supplied by the vaccinia p11 coding sequence. The resulting recombinant plasmid was used to introduce the CT99 sequence into the vaccinia virus genome using methods described by Cochran et al. (Proc. Natl. Acad. Sci. USA 82: 19, 1985) and Chakrabarti et al. (Mol. Cell Biol. 5: 3403, 1985). The VV99 virus isolate was plaque purified several times, amplified into stocks, and tested for the presence of the inserted βAPP sequence by Southern blot analysis. Western blot analysis documented that the VV99 was expressing CT99 (Wolf et al. ibid).

To produce membranes containing high levels of CT99, ~$10^9$ CV-1 monkey fibroblast cells were infected with VV99 for 48 hours. After this period, the cells were harvested, washed with saline, and pelleted by low speed centrifugation at 1200 rpm for 10 minutes at 4° C. The cell pellet was resuspended in 25 mls 0.25 M sucrose, 10 mM Tris-HCl pH 7.5, 1 mM EDTA then homogenized with a Dounce homogenizer using a tight fitting pestle. The sample is centrifuged at 2300 rpm for 10 minutes at 4° C. This homogenization step was repeated.

The resulting pellets containing nuclei and large debris were discarded and the post-nuclear supernatants were combined. The supernatant fraction was centrifuged at 100,000×g for 30–60 minutes at 4° C. to collect membranes. The membranes were washed in buffer containing 0.2% saponin, 10 mM Tris-HCl pH 7.5, 1 mM EDTA to remove contaminating proteolytic activity, followed by centrifugation at 100,000×g for 30 minutes at 4° C. This step was repeated. Membranes at this stage can be used directly for assaying γ-secretase activity, or may be further treated to provide solubilized γ-secretase activity.

The saponin-washed membrane fraction was next solubilized with 0.5% CHAPS prepared in 10 mM Tris-HCl pH 7.5 with 5 mM EDTA. Aliquots of membranes containing γ-secretase activity were treated with detergent at 0° C. for 1 hour after which the treated samples were centrifuged at 100,000×g for 1 hour at 4° C. The resulting supernatants (soluble fractions) were assayed for Aβ production. 0.5% CHAPS was successful in solubilizing and preserving the γ-secretase activity.

Both the saponin-washed membrane fraction and the 0.5% CHAPS solubilized fraction described above can be used as a source of CT99 substrate and γ-secretase activity for the assay. CT99 substrate is present in both of these fractions, as shown by Western blot, and when incubated with the appropriate enzymes can be processed to Aβ (see Examples 2 & 3 below). Both the saponin-washed fraction and the CHAPS solubilized fraction can be stored at −80° C. without loss of activity upon thawing.

Figure 2:
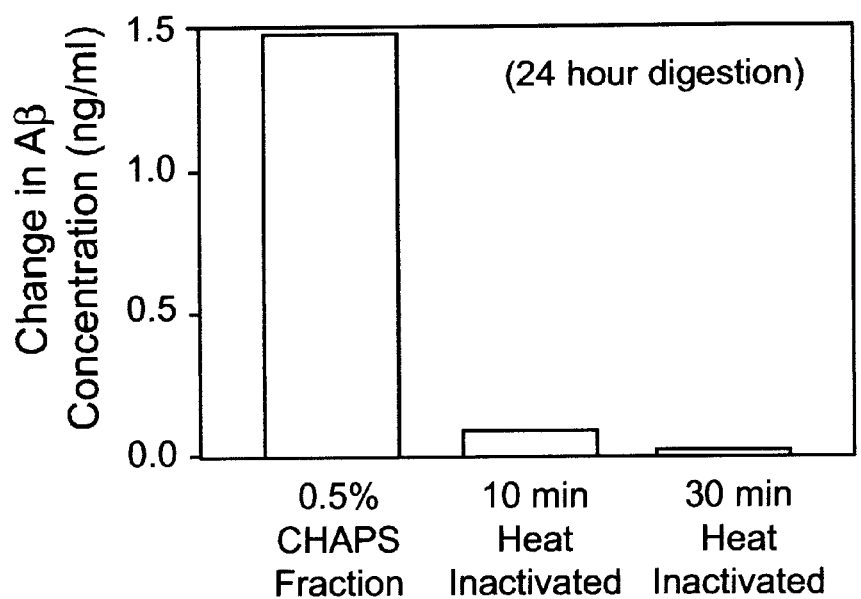
FIG. 2 is a bar graph illustrating the heat inactivation of soluble γ-secretase activity.

The γ-secretase activity present in the membrane extract or solubilized from the membrane had a pH optimum near neutrality, as shown in FIG. 1. Suppression of Aβ production was seen at lower pH conditions, such as pH 4.0 or 5.0. In contrast, pH 6.0 and 7.0 showed the largest production of Aβ by the extract with pH 8.0 giving slightly lower levels. The solubilized γ-secretase activity was also heat sensitive, indicating that it is a protein(s). Treating the sample at 100° C. for 10 or 30 minutes eliminated essentially all of the Aβ generating activity (FIG. 2).

Example 2.
Production of Aβ by Cell-Free γ-secretase System.

To produce Aβ protein in vitro, an aliquot of the saponin-washed fraction or an aliquot of the 0.5% CHAPS treated soluble fraction was first adjusted to pH 7.0 by making a 1:10 dilution of the fraction with 1 M Tris-HCl pH 7.0 for a final concentration of 100mM Tris-HC1. The neutralized samples were incubated at 37° C. for various lengths of time, typically ranging from 0 (control) to 24 hours. After incubation, the samples were assayed for Aβ production as follows.

Wells of a 96-microtiter plate were coated overnight at 4° C. with 100 μl/well of a 4 μg/ml solution of purified monoclonal antibody 1702.1 diluted in phosphate buffered saline (PBS). The 1702.1 monoclonal antibody specifically recognizes the Aβ40 isoform. The plate was washed three time with PBS containing 0.05% Tween-20, and the wells treated with 1% bovine serum albumin (BSA) for 1 hour at 37° C. to block non-specific protein interactions. The plate was washed following incubation with BSA. The test sample was diluted to 100 μl in PBS, 0.05% Tween 20, 0.1% BSA and added to each well of the plate. The plate was incubated at 4° C. overnight or at 37° C. for 2 hours. After this incubation, the plate was washed three times with PBS 0.05% Tween 20. One hundred μl of a biotinylated second Aμ monoclonal antibody, 1101.1, diluted in PBS, 0.05% Tween 20 and 0.1% BSA is added to each well and the plate is incubated at 37° C. for 2 hours. The plate is washed three times with PBS 0.05% Tween 20 and the amount of 1101.1 second antibody bound to the well is detected with HRP-conjugated Streptavidin (Zymed) using a tetramethylbenzidine substrate (Sigma). The resulting colorimetric reaction is quantified by reading the plate at $OD^{450nm}$. The amount of Aβ40 present in the test sample is calculated from known amounts of synthetic Aβ40 peptide standard run in the ELISA.

Figure 3:
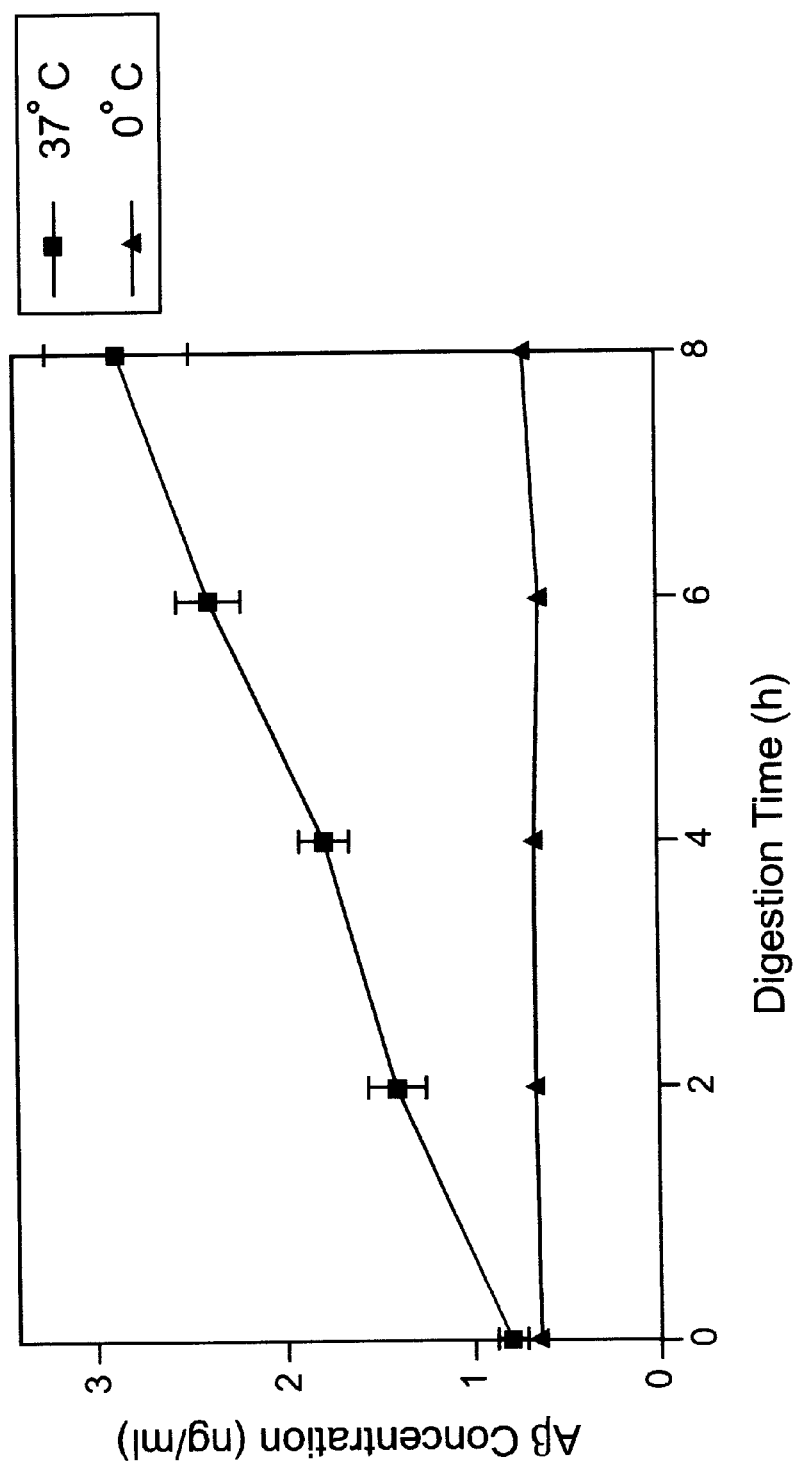
FIG. 3 is a line graph illustrating the production of $A\beta_{40}$ by the solubilized γ-secretase activity.

FIG. 3 shows the production of Aβ40 by the solubilized γ-secretase extract prepared as described in Example 1. Ten μl aliquots of γ-secretase were incubated at 37° C. for various periods of time ranging from 0 to 8 hours. After incubation, the samples were diluted in assay buffer (PBS, 0.05% Tween 20, 0.1% BSA) and the Aβ40 present was quantified with the ELISA. A linear production over the test time period was obtained, indicating that Aβ40 was generated by incubation of the solubilized γ-secretase activity.

Alternatively, Western blot analysis can be used to monitor Aβ generation by the solubilized γ-secretase. The sample was diluted in Laemmli buffer and electrophoresed on a 16% Tris-tricine polyacylamide gel. Proteins separated on the gel were transferred electrophoretically to a 0.2 micron nitrocellulose membrane. The membrane was rinsed three times in PBS, immersed in PBS and boiled for 6 minutes. The treated membrane was used in a standard Western blot assay. The generation of Aβ was shown using a Western blot analysis and an Aβ-specific monoclonal antibody (Ida et al. J. Biol. Chem. 271: 22908, 1996). Immunoprecipitation of the Aβ can also be used to detect product.

Figure 4:
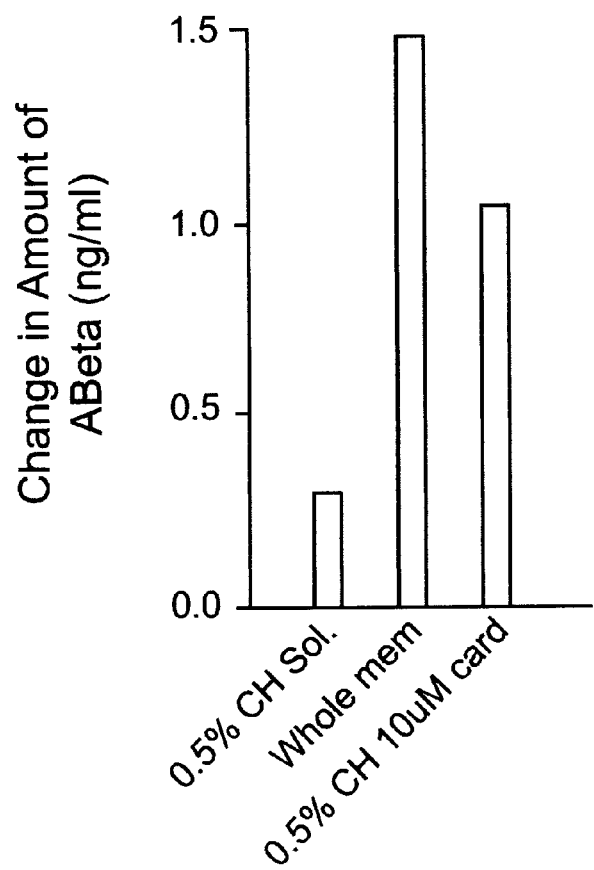
FIG. 4 is a bar graph illustrating the ability of cardiolipin to enhance the γ-secretase activity of the assay.

The 0.5% CHAPS solubilized γ-secretase activity can be augmented by the addition of synthetic phospholipids. See FIG. 4. The enhancement of γ-secretase activity by addition of 1 μM cardiolipin (Sigma) is nearly equivalent to the activity originally present in the membranes prior to solubilization. Other phospholipids, such as phosphotidylcholine, phosphotidylserine, and 1,2 dipalmitoyl-5-glycerol-3-phosphocholine, were also tested with comparable results.

Example 3.
Reconstitution of γ-secretase Activity with CT100

Solubilized γ-secretase was prepared from membranes of wild-type cells, i.e. cells not genetically manipulated for βAPP or CT100 expression. The γ-secretase activity was independently prepared as described above in Example 1, and combined with purified CT100. The CT100 was produced by in vitro transcription and translation system (Ambion) from an appropriate expression plasmid in prokaryoptic or eukaroytic cells expressing CT100 by transient or stable transfection. The CT100 substrate can be radiolabeled using this method and/or the CT100 can bear an epitope tag at its carboxyl-terminus to facilitate purification using immunoaffinity methods.

Figure 5:
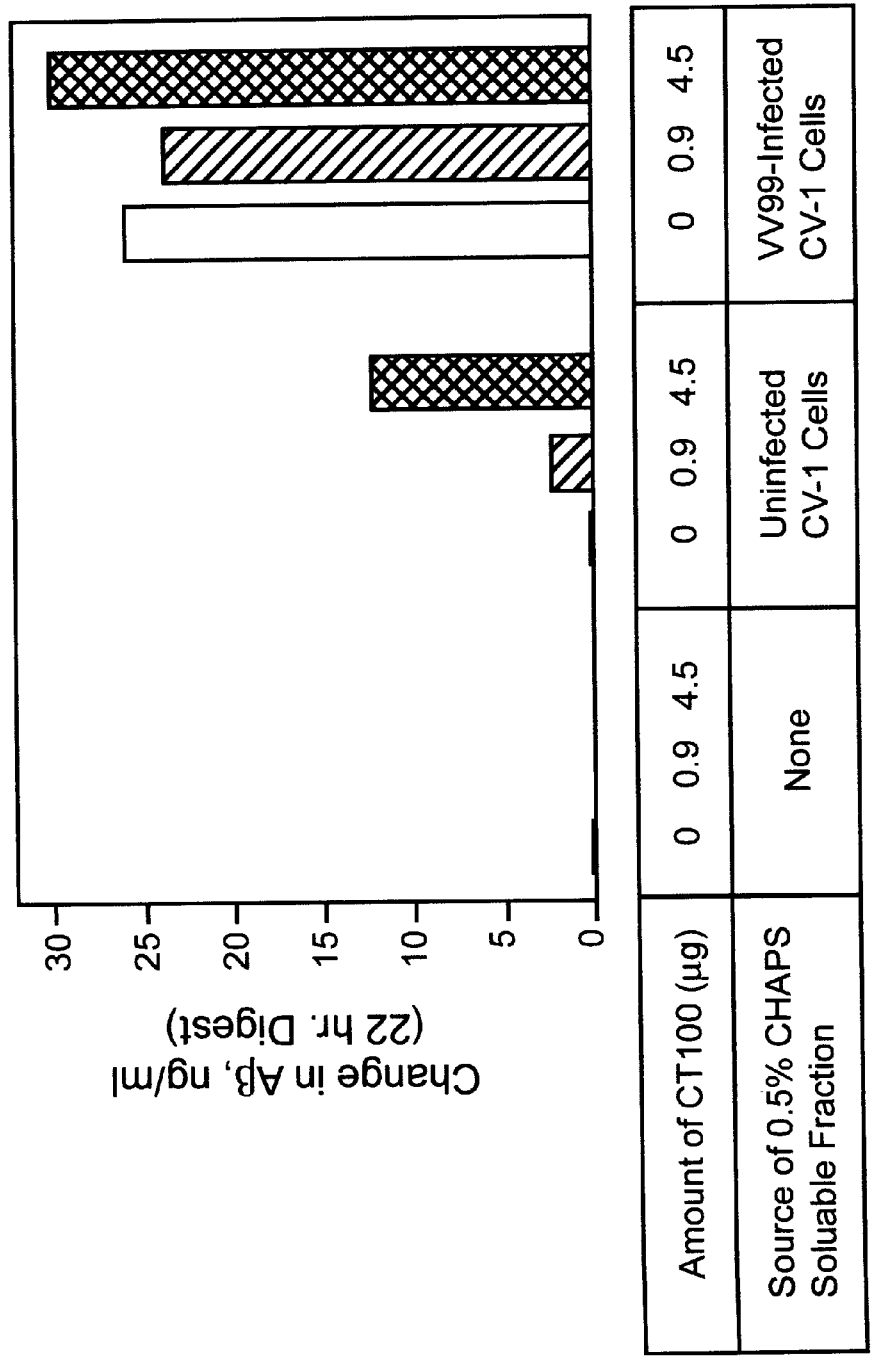
FIG. 5 is a bar graph illustrating the activity of reconstituted γ-secretase activity and CT100.

The γ-secretase is mixed with CT100 substrate and the reconstituted mixture is incubated 37° C. for various periods to generate Aβ, which is the detected proteolytic product produced from γ-secretase cleavage of CT100 (FIG. 5). This shows that the γ-secretase activity can be reconstituted by combining separate fractions containing enzymatic activity and substrate.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated preparation having γ-secretase activity comprising a solubilized amyloid precursor protein (APP)/γ-secretase and CT99 mixture, wherein said activity is characterized by the ability to produce Aβ in vitro.

2. The preparation of claim 1, wherein the preparation comprises isolated γ-secretase activity reconstituted with APP or an APP proteolytic product.

3. The preparation of claim 1, wherein the APP/γ-secretase mixture comprises an APP having a mutation which increases γ-secretase activity.

4. The preparation of claim 3, wherein the APP mutation is the "Swedish" mutation of APP (K595N/M596L).

5. The preparation of claim 1, wherein the preparation further comprises a synthetic phospholipid.

6. The preparation of claim 5, wherein said synthetic phospholipid is a cardiolipin.

* * * * *